United States Patent [19]

Ahle

[11] Patent Number: 4,664,699
[45] Date of Patent: May 12, 1987

[54] METHOD OF IMPROVING RESIDUAL HERBICIDAL ACTIVITY AND COMPOSITIONS

[75] Inventor: James L. Ahle, San Jose, Calif.

[73] Assignee: Stauffer Chemical Company, Westport, Conn.

[21] Appl. No.: 699,165

[22] Filed: Feb. 7, 1985

[51] Int. Cl.⁴ .................. A01N 37/44; A01N 37/22
[52] U.S. Cl. ................................ 71/100; 71/88; 71/94; 71/111; 71/118
[58] Field of Search .................................. 71/100, 118

[56] References Cited

U.S. PATENT DOCUMENTS

| | | | |
|---|---|---|---|
| 3,175,897 | 3/1965 | Tilles | 71/100 |
| 3,547,620 | 12/1970 | Olin | 71/118 |
| 4,003,735 | 1/1977 | Czajkowski et al. | 71/118 |
| 4,146,387 | 3/1979 | Thiele | 71/118 |
| 4,378,990 | 4/1983 | Endo et al. | 71/118 |

FOREIGN PATENT DOCUMENTS 2444406 8/1980 France ................................ 71/118

Primary Examiner—Glennon H. Hollrah
Assistant Examiner—P. Morris
Attorney, Agent, or Firm—Paul R. Martin

[57] ABSTRACT

Herbicide combinations with improved residual activity comprising (a) compounds of the formula

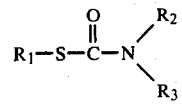

wherein $R_1$ is selected from the group consisting of lower alkyl having from 2 to 6 carbon atoms, haloalkyl, benzyl and substituted benzyl, phenethyl, pyridylmethyl, cycloalkyl having from 3 to 6 carbon atoms, and haloalkenyl having from 3 to 6 carbon atoms, and $R_2$ and $R_3$ are each independently selected from the group consisting of $C_2$-$C_6$ alkyl, $C_2$-$C_6$ alkenyl, and $C_3$-$C_8$ cycloalkyl, provided further that $R_2$ and $R_3$ can join with the nitrogen to which they are attached to form a 5 to 6 carbon ring structure, and (b) an herbicidally effective amount of a chloroacetanilide having the formula

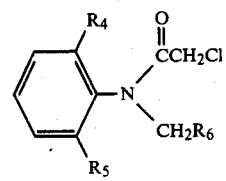

in which $R_4$ is a straight or branched chain lower alkyl group having from 1 to 6 carbon atoms; $R_5$ is a straight or branched chain lower alkyl group having from 1 to 6 carbon atoms; and $R_6$ is

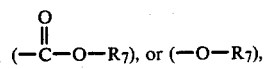

where $R_7$ is a straight or branched chain lower alkyl group having from 1 to 6 carbon atoms.

1 Claim, No Drawings

METHOD OF IMPROVING RESIDUAL HERBICIDAL ACTIVITY AND COMPOSITIONS

BACKGROUND OF THE INVENTION

Herbicides are widely used by farmers and commercial agricultural companies in order to increase crop yields for such staple crops as corn, soybeans, rice and the like.

Herbicides are effective in killing or controlling weeds and grasses which compete for soil nutrients with the crop plants. One particularly successful herbicide is RO-NEET ®, a herbicide of the thiocarbamate type, which is used for the control of weeds in pre-plant sugarbeets, spinach and table beets, particularly. The thiocarbamates are used extensively at the present time.

Not all weeds germinate at the same time or at the same rate. Accordingly, a specific herbicide which may be effective against weeds which germinate at or about the same time as the crop plant, may not be quite as effective against late-germinating weeds. The residual activity of the herbicide against late-germinating weeds leaves something to be desired. One such late-germinating weed is wild proso millet, which is conventionally found in the environment of corn and soybean crop plants.

It would be advantageous to find a method of extending the residual activity of specific herbicides, and that is what this invention is concerned with.

DESCRIPTION OF THE INVENTION

It has now been discovered that the residual activity of thiocarbamate herbicides as represented by RO-NEET ®, and others of the same type, can be extended by combining that herbicide with an additional herbicide of the chloroacetanilide type as further defined herein.

The composition of this invention comprises (a) a herbicidally effective amount of a thiocarbamate having the formula $$R_1-S-\overset{O}{\overset{\|}{C}}-N\overset{R_2}{\underset{R_3}{\diagdown}}$$

wherein $R_1$ is selected from the group consisting of lower alkyl having from 2 to 6 carbon atoms, haloalkyl, benzyl and substituted benzyl, phenethyl, pyridylmethyl, cycloalkyl having from 3 to 6 carbon atoms, and haloalkenyl having from 3 to 6 carbon atoms, and $R_2$ and $R_3$ are each independently selected from the group consisting of $C_2$-$C_6$ alkyl, $C_2$-$C_6$ alkenyl, and $C_3$-$C_8$ cycloalkyl, provided further that $R_2$ and $R_3$ can join with the nitrogen to which they are attached to form a 5 to 6 carbon ring structure, and (b) a herbicidally effective amount of a chloroacetanilide having the formula

[structure: benzene ring with $R_4$ and $R_5$ substituents, N attached to $CCH_2Cl$ (C=O) and $CH_2R_6$]

in which $R_4$ is a straight or branched chain lower alkyl group having from 1 to 6 carbon atoms;

$R_5$ is a straight or branched chain lower alkyl group having from 1 to 6 carbon atoms; and $R_6$ is $$(-\overset{O}{\overset{\|}{C}}-O-R_7), \text{ or } (-O-R_7),$$

where $R_7$ is a straight or branched chain lower alkyl group having from 1 to 6 carbon atoms.

This invention also relates to a method for extending the residual activity of herbicides which comprises applying to the locus where control is desired, a herbicidal composition comprising:

(a) a herbicidally effective amount of a thiocarbamate having the formula $$R_1-S-\overset{O}{\overset{\|}{C}}-N\overset{R_2}{\underset{R_3}{\diagdown}}$$

wherein $R_1$ is selected from the group consisting of lower alkyl having from 2 to 6 carbon atoms, haloalkyl, benzyl and substituted benzyl, phenethyl, pyridylmethyl, cycloalkyl having from 3 to 6 carbon atoms, and haloalkenyl having from 3 to 6 carbon atoms, and $R_2$ and $R_3$ are each independently selected from the group consisting of $C_2$-$C_6$ alkyl, $C_2$-$C_6$ alkenyl, and $C_3$-$C_8$ cycloalkyl, provided further that $R_2$ and $R_3$ can join with the nitrogen to which they are attached to form a 5 to 6 carbon ring structure, and (b) a herbicidally effective amount of a chloroacetanilide having the formula

[structure: benzene ring with $R_4$ and $R_5$ substituents, N attached to $CCH_2Cl$ (C=O) and $CH_2R_6$]

in which $R_4$ is a straight or branched chain lower alkyl group having from 1 to 6 carbon atoms;

$R_5$ is a straight or branched chain lower alkyl group having from 1 to 6 carbon atoms; and $R_6$ is $$(-\overset{O}{\overset{\|}{C}}-O-R_7), \text{ or } (-O-R_7),$$

where $R_7$ is a straight or branched chain lower alkyl group having from 1 to 6 carbon atoms.

The term "alkyl" is used herein in its normal meaning and is intended to include both straight- and branched-chain groups.

The term "herbicide", as used herein, means a compound or composition which controls or modifies the growth of plants. By the term "herbicidally effective amount" is meant any amount of such compound or composition which causes a modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing and the like.

Within the scope of the present invention, certain embodiments are preferred, namely:

In the thiocarbamates, $R_1$ is preferably ethyl or n-propyl, $R_2$ is preferably ethyl, and $R_3$ is preferably n-butyl or cyclohexyl.

In the anilides, $R_4$ is preferably methyl, $R_5$ is preferably ethyl, $R_6$ is preferably (—O—$R_7$), and $R_7$ is preferably ethyl.

The thiolcarbamates within the scope of the present invention can be prepared by the processes described in U.S. Pat. No. 2,913,327 (Tilles et al., Nov. 17, 1959), and U.S. Pat. No. 3,185,720 (Tilles et al., May 25, 1965).

The chloroacetanilide compounds used in the synergistic combinations of the invention can be purchased commercially.

The preferred thiolcarbamate compound for use in this invention is S-ethyl N-ethyl thiocyclohexanecarbamate (RO-NEET ®).

Other representative thiolcarbamate compounds suitable for use as herbicides in the compositions and method of the invention include S-ethyl N,N-dipropyl thiolcarbamate, S-ethyl N,N-diisobutyl thiolcarbamate, S-propyl N,N-dipropyl thiolcarbamate, S-2,3,3-trichloroallyl N,N-diisopropyl thiolcarbamate, S-ethyl cyclohexylethyl thiolcarbamate, S-ethyl hexadydro-1H-azepine-1-carbothioate, and n-propyl ethyl-n-butyl-thiolcarbamate.

Specific chloroacetanilide compounds which have been found to be effective in the compositions of the present invention, include, for example: acetochlor, 2-chloro-2'-methyl-6'-ethyl-N-methoxymethyl acetanilide; alachlor, 2-chloro-2',6'-diethyl-N-(methoxymethyl)acetanilide; dithatyl ethyl, N-chloroacetyl-N-(2,6-diethylphenyl)-glycine ethyl ester; and butachlor, N-(butoxymethyl)-2-chloro-2',6'-diethyl acetanilide.

In the compositions of this invention, the (thiolcarbamate):(anilide) weight ratio lies within the following approximate limits, in order of increasing preference: 0.01:1 to 50:1; 0.05:1 to 32:1; 0.1:1 to 20:1; and 1:1 to 10:1.

The variety of crops on which the present herbicidal composition is useful can be significantly broadened by the use of an antidote to protect the crop from injury and render the composition more selective against weeds.

For antidote descriptions and methods of use, reference is made to U.S. Pat. No. 3,959,304, issued to E. G. Teach on May 25, 1976; U.S. Pat. No. 3,989,503, issued to F. M. Pallos et al. on Nov. 2, 1976; U.S. Pat. No. 4,021,224, issued to F. M. Pallos et al. on May 3, 1977; U.S. Pat. No. 3,131,509 issued to O. L. Hoffman on May 5, 1964; and U.S. Pat. No. 3,564,768, issued to O. L. Hoffman on Feb. 3, 1971.

Examples of useful antidotes include acetamides such as N,N-diallyl-2,2-dichloroacetamide and N,N-diallyl-2-chloroacetamide, oxazolidines such as 2,2,5-trimethyl-N-dichloroacetyl oxazolidine and 2,2-spirocyclohexane-N-dichloroacetyl oxazolidine, and 1,8-naphthalic anhydride. For maximum effect, the antidote is present in the composition in a non-phytotoxic, antidotally effective amount. By "non-phytotoxic" is meant an amount which causes at most minor injury to the crop. By "antidotally effective" is meant an amount which substantially decreases the extent of injury caused by the herbicide to the crop. The preferred weight ratio of herbicide to antidote is about 0.1:1 to about 30:1. The most preferred range for this ratio is about 3:1 to about 20:1.

Herbicidal compositions illustrative of those embodied in the instant application were prepared and evaluated for herbicidal effect. The results are shown in the following examples.

EXAMPLE 1

Twenty-six treatments of various herbicides were evaluated for extension of sufficient residual activity to control wild proso millet and other weed pests over an eight week period.

For each treatment, 16 aluminum loaf pans, $7\frac{3}{8} \times 3\frac{7}{8} \times 2.5$ deep were filled with moist sandy loam soil from the Livermore, Calif. area. The soil was screened and 17-17-17 fertilizer was added. All 16 flats were sprayed at one pass on a linear spray table at a volume of 25 gal/acre. When the thiocarbamate herbicides were applied alone the rate was 4 lb/A; in combinations the rate was 3 lb/A of the thiocarbamates and 1 lb/A of the chloroacetanilides. Within 5 minutes after spraying, the sprayed soil from all 16 trays was dumped into a small cement mixer and incorporated, i.e., mixed up for a minimum of 3 minutes. After incorporation, the soil was placed in ½ bushel size plastic tubs. Three flats of each treatment were seeded the next day after treatment. The tubs with the remainder of the soil were set aside and kept moist. The temperature was maintained at 78° F. during the day and 70° F. overnight. Every two weeks, three more flats were seeded. On the day of every seeding, the soil was thoroughly mixed again. RO-NEET ® was applied at ½ and 1 lb/A on each seeding date; this was for determining the amount of residual activity kept in the soil. The results of these tests are set forth in the table below.

TABLE I

| Cmpd. No. | Corn | | | | Corn-1 | | | | Wild Proso Millet | | | |
|---|---|---|---|---|---|---|---|---|---|---|---|---|
| | 1 | 2 | 3 | AVG | 1 | 2 | 3 | AVG | 1 | 2 | 3 | AVG |
| First Planting % Control | | | | | | | | | | | | |
| 1 | 0 | 0 | 0 | 0 | 0 | 0 | 0 | 0 | 100 | 98 | 100 | 99 |
| 2 | 10 | 0 | 0 | 3 | 0 | 0 | 0 | 0 | 80 | 90 | 90 | 87 |
| 3 | 0 | 10 | 0 | 3 | 0 | 0 | 0 | 0 | 100 | 100 | 100 | 100 |
| Second Planting % Control | | | | | | | | | | | | |

TABLE I-continued

| Cmpd. No. | 1 | 2 | 3 | | 1 | 2 | 3 | AVG | | 1 | 2 | 3 | AVG |
|---|---|---|---|---|---|---|---|---|---|---|---|---|---|
| 1 | 20 | 20 | 10 | 17 | 0 | 0 | 0 | 0 | 95 | 95 | 95 | 95 |
| 2 | 10 | 10 | 10 | 10 | 0 | 10 | 10 | 7 | 95 | 95 | 98 | 96 |
| 3 | 10 | 10 | 10 | 10 | 10 | 0 | 10 | 7 | 100 | 100 | 100 | 100 |
| Third Planting % Control |
| 1 | 0 | 0 | 0 | 0 | 0 | 0 | 0 | 0 | 80 | 80 | 70 | 77 |
| 2 | 0 | 0 | 0 | 0 | 0 | 0 | 0 | 0 | 80 | 90 | 80 | 83 |
| 3 | 0 | 0 | 0 | 0 | 0 | 0 | 0 | 0 | 95 | 98 | 95 | 96 |
| Fourth Planting % Control |
| 1 | 20 | 10 | 10 | 13 | 0 | 0 | 0 | 0 | 60 | 70 | 60 | 63 |
| 2 | 0 | 0 | 0 | 0 | 0 | 0 | 0 | 0 | 60 | 80 | 60 | 67 |
| 3 | 0 | 0 | 10 | 3 | 0 | 0 | 0 | 0 | 98 | 98 | 98 | 98 |
| Fifth Planting % Control |
| 1 | 0 | 0 | — | 0 | 0 | 0 | — | 0 | 50 | 30 | — | 40 |
| 2 | 0 | 0 | — | 0 | 0 | 0 | — | 0 | 60 | 70 | — | 65 |
| 3 | 0 | 10 | 10 | 7 | 0 | 0 | 0 | 0 | 100 | 100 | 100 | 100 |

| Cmpd. No. | Green Foxtail | | | | Barnyardgrass | | | | Wild Oats | | | |
|---|---|---|---|---|---|---|---|---|---|---|---|---|
| | 1 | 2 | 3 | AVG | 1 | 2 | 3 | AVG | 1 | 2 | 3 | AVG |
| First Planting % Control |
| 1 | 98 | 98 | 100 | 99 | 98 | 98 | 100 | 99 | 100 | 100 | 100 | 100 |
| 2 | 100 | 100 | 100 | 100 | 100 | 100 | 100 | 100 | 100 | 90 | 100 | 97 |
| 3 | 100 | 100 | 100 | 100 | 100 | 100 | 100 | 100 | 100 | 100 | 100 | 100 |
| Second Planting % Control |
| 1 | 100 | 100 | 100 | 100 | 95 | 98 | 100 | 98 | 100 | 100 | 100 | 100 |
| 2 | 100 | 100 | 100 | 100 | 100 | 100 | 100 | 100 | 100 | 98 | 90 | 96 |
| 3 | 100 | 100 | 100 | 100 | 100 | 100 | 100 | 100 | 100 | 100 | 100 | 100 |
| Third Planting % Control |
| 1 | 90 | 80 | 90 | 87 | 90 | 90 | 90 | 90 | 100 | 85 | 98 | 99 |
| 2 | 100 | 100 | 100 | 100 | 80 | 90 | 100 | 90 | 95 | 100 | 100 | 98 |
| 3 | 100 | 100 | 100 | 100 | 100 | 100 | 100 | 100 | 100 | 100 | 100 | 100 |
| Fourth Planting % Control |
| 1 | 80 | 80 | 80 | 80 | 90 | 95 | 90 | 92 | 90 | 98 | 90 | 93 |
| 2 | 95 | 100 | 95 | 97 | 100 | 100 | 95 | 98 | 80 | 90 | 90 | 87 |
| 3 | 100 | 100 | 100 | 100 | 100 | 100 | 100 | 100 | 100 | 100 | 100 | 100 |
| Fifth Planting % Control |
| 1 | 50 | 50 | — | 50 | 80 | 90 | — | 85 | 100 | 80 | — | 90 |
| 2 | 100 | 100 | — | 100 | 100 | 100 | — | 100 | 80 | 90 | — | 85 |
| 3 | 100 | 100 | 100 | 100 | 100 | 100 | 100 | 100 | 100 | 90 | 90 | 93 |

1 = RO-NEET ® (S—ethyl N—ethyl thiocyclohexane carbamate)
2 = 2-t-butyl, 6-methyl-N—n-propoxymethyl-α-chloroacetanilide
3 = The combination of Compounds 1 and 2.

As seen from the results set forth above, the thiocarbamate defined herein and as represented by the commercial product RO-NEET ® shows more residual activity for controlling wild proso millet when combined with the chloroacetanilides of this invention than either product does alone.

EXAMPLE 2

Another series of tests was conducted for the purpose of evaluating the combination of RO-NEET ® with another chloroacetanilide which is preferred for use in the compositions of this invention, for extension of sufficient residual activity to control wild proso millet over a 12-week period. For each treatment 16 aluminum loaf pans, $7\frac{7}{8} \times 7\frac{7}{8} \times 2\frac{1}{2}$ inches deep were filled with moist Keeton sandy loam soil. The soil was screened and 17-17-17 fertilizer was added. All sixteen flats were sprayed at one pass in the linear spray table at a volume of 25 gal/acre. Most of the RO-NEET ® rates were 4 lb/A. Within five minutes after spraying, the sprayed soil from all 16 pans was dumped into a small cement mixer and incorporated (mixed) for a minimum of 3 minutes. After incorporation, the soil was placed in ½ bushel size plastic tubs. Three flats of each treatment were seeded the next day. The tubs with the remainder of the soil were placed in a secure location and kept moist. The temperature was 78° F. during the day and 70° F. at night. Every three weeks, three more flats were seeded. On the day of every seeding, the soil was thoroughly mixed before placing in the pans.

The various weed species against which the combinations were tested are as follows: shattercane (*Sorghum bicolor*), velvetleaf (*Abutilon theophrasti*), giant foxtail (*Setaria faberi*) and wild proso millet (RM) (*Panicum miliaceum*).

In addition, the combinations were tested against two varieties of corn for comparative purposes.

Each test solution contained an antidote in an amount sufficient to protect the crop plants (0.33 lb/A).

The results of these tests are set forth in Table II below.

TABLE II

| Cmpd. No. | Rate (lb/A) | Corn | | | | Corn-1 | | | | Shattercane | | | |
|---|---|---|---|---|---|---|---|---|---|---|---|---|---|
| | | 1 | 2 | 3 | AVG | 1 | 2 | 3 | AVG | 1 | 2 | 3 | AVG |
| First Planting % Control |
| 4 | 4 | 0 | 0 | 0 | 0 | 0 | 0 | 0 | 0 | 100 | 100 | 100 | 100 |
| 5 | 1 | 0 | 0 | 0 | 0 | 0 | 0 | 0 | 0 | 70 | 80 | 90 | 80 |
| 6 | 4 + 1 | 10 | 0 | 0 | 3 | 10 | 0 | 0 | 3 | 100 | 100 | 100 | 100 |
| Second Planting % Control |
| 4 | 4 | 0 | 0 | 0 | 0 | 0 | 0 | 0 | 0 | 98 | 100 | 100 | 99 |
| 5 | 1 | 0 | 0 | 0 | 0 | 0 | 0 | 0 | 0 | 98 | 100 | 100 | 99 |

TABLE II-continued

| Cmpd No. | Rate (lb/A) | 1 | 2 | 3 | AVG | 1 | 2 | 3 | AVG | 1 | 2 | 3 | AVG |
|---|---|---|---|---|---|---|---|---|---|---|---|---|---|
| 6 | 4 + 1 | 10 | 0 | 0 | 3 | 0 | 0 | 0 | 0 | 98 | 100 | 100 | 99 |
| Third Planting % Control ||||||||||||||
| 4 | 4 | 0 | 0 | 0 | 0 | 0 | 0 | 0 | 0 | 95 | 98 | 98 | 97 |
| 5 | 1 | 0 | 0 | 0 | 0 | 0 | 0 | 0 | 0 | 98 | 95 | 95 | 96 |
| 6 | 4 + 1 | 0 | 0 | 0 | 0 | 0 | 0 | 0 | 0 | 98 | 100 | 98 | 99 |
| Fourth Planting % Control ||||||||||||||
| 4 | 4 | 0 | 0 | 0 | 0 | 0 | 0 | 0 | 0 | 40 | 50 | 40 | 43 |
| 5 | 1 | 0 | 0 | 0 | 0 | 0 | 0 | 0 | 0 | 80 | 80 | 90 | 83 |
| 6 | 4 + 1 | 0 | 0 | 0 | 0 | 0 | 0 | 0 | 0 | 90 | 80 | 80 | 83 |
| Fifth Planting % Control ||||||||||||||
| 4 | 4 | 0 | 0 | 0 | 0 | 0 | 0 | 0 | 0 | 10 | 0 | 0 | 3 |
| 5 | 1 | 0 | 0 | 0 | 0 | 0 | 0 | 0 | 0 | 90 | 80 | 80 | 83 |
| 6 | 4 + 1 | 0 | 0 | 0 | 0 | 0 | 0 | 0 | 0 | 95 | 90 | 80 | 88 |

| Cmpd No. | Rate (lb/A) | Velvetleaf ||||  Giant Foxtail |||| Wild Proso Millet ||||
|---|---|---|---|---|---|---|---|---|---|---|---|---|---|
| | | 1 | 2 | 3 | AVG | 1 | 2 | 3 | AVG | 1 | 2 | 3 | AVG |
| First Planting % Control ||||||||||||||
| 4 | 4 | 100 | 100 | 100 | 100 | — | — | — | — | 98 | 98 | 100 | 99 |
| 5 | 1 | 50 | 50 | 50 | 50 | — | — | — | — | 80 | 60 | 80 | 73 |
| 6 | 4 + 1 | 100 | 100 | 100 | 100 | — | — | — | — | 90 | 95 | 90 | 92 |
| Second Planting % Control ||||||||||||||
| 4 | 4 | 100 | 80 | 100 | 93 | 100 | 90 | 95 | 95 | 90 | 90 | 100 | 93 |
| 5 | 1 | 50 | 70 | 80 | 67 | 100 | 100 | 100 | 100 | 98 | 98 | 95 | 97 |
| 6 | 4 + 1 | 98 | 98 | 100 | 99 | 100 | 100 | 100 | 100 | 100 | 98 | 98 | 99 |
| Third Planting % Control ||||||||||||||
| 4 | 4 | 70 | 60 | 60 | 63 | 98 | 98 | 95 | 97 | 80 | 80 | 90 | 83 |
| 5 | 1 | 50 | 50 | 60 | 53 | 98 | 100 | 100 | 99 | 80 | 80 | 90 | 83 |
| 6 | 4 + 1 | 80 | 80 | 80 | 80 | 100 | 100 | 100 | 100 | 95 | 98 | 90 | 94 |
| Fourth Planting % Control ||||||||||||||
| 4 | 4 | 20 | 40 | 20 | 27 | 50 | 70 | 50 | 57 | 10 | 20 | 10 | 13 |
| 5 | 1 | 0 | 10 | 10 | 7 | 100 | 95 | 100 | 98 | 70 | 50 | 60 | 60 |
| 6 | 4 + 1 | 20 | 20 | 10 | 17 | 100 | 100 | 100 | 100 | 70 | 80 | 80 | 77 |
| Fifth Planting % Control ||||||||||||||
| 4 | 4 | 10 | 0 | 0 | 3 | 50 | 20 | 20 | 30 | 20 | 20 | 10 | 17 |
| 5 | 1 | 10 | 10 | 10 | 10 | 90 | 80 | 90 | 87 | 50 | 40 | 60 | 50 |
| 6 | 4 + 1 | 10 | 10 | 10 | 10 | 95 | 100 | 100 | 98 | 60 | 70 | 70 | 67 |

4 = RO-NEET ® (S—ethyl N—ethyl thiocyclohexane carbamate)
5 = 2-chloro-1'-methyl-6'-ethyl-N—ethoxymethyl acetanilide
6 = The combination of Compounds 4 and 5.

METHODS OF APPLICATION

The herbicidal compositions of the present invention are useful in controlling the growth of undesirable vegetation by pre-emergence or post-emergence application to the locus where control is desired, including pre-plant, soil surface and post-emergence applications. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfate or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid)taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates used in the present invention will consist of from about 15 to about 90 weight percent active material, about 10 to 85 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with macroscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15-30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide composition together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. A method of controlling wild proso millet which consists essentially of applying to the locus where control is desired a herbicidally effective amount of a herbicidal composition consisting essentially of
   (a) an herbicidally effective amount of S-ethyl N-ethylthiocyclohexanecarbamate and
   (b) an herbicidally effective amount of 2-t-butyl, 6-methyl-N-n-propoxymethyl-$\alpha$-chloroacetanilide additionally in the presence of an antidotally effective amount of 2,2,5-trimethyl-N-dichloroacetyl oxazolidine.

* * * * *